United States Patent [19]

Maingault

[11] Patent Number: 5,981,497
[45] Date of Patent: Nov. 9, 1999

[54] UTILIZATION OF SOPHOROLIPIDS AS THERAPEUTICALLY ACTIVE SUBSTANCES OR COSMETIC PRODUCTS, IN PARTICULAR FOR THE TREATMENT OF THE SKIN

[75] Inventor: Martine Maingault, Saint Macaire du Bois, France

[73] Assignee: Institut Francais du Petrole, Rueil-Malmaison Cedex, France

[21] Appl. No.: 08/981,606

[22] PCT Filed: Jun. 25, 1996

[86] PCT No.: PCT/FR96/00991

§ 371 Date: Jan. 29, 1999

§ 102(e) Date: Jan. 29, 1997

[87] PCT Pub. No.: WO97/01343

PCT Pub. Date: Jan. 16, 1997

[30] Foreign Application Priority Data

Jun. 28, 1995 [FR] France .................................. 95 08085

[51] Int. Cl.⁶ ............................. A01N 43/04; A61K 31/70
[52] U.S. Cl. ............................. 514/25; 514/53; 514/885; 514/886; 514/928; 514/969
[58] Field of Search ................................ 514/25, 53, 885, 514/886, 928, 969

[56] References Cited

U.S. PATENT DOCUMENTS

3,312,684 4/1967 Spencer et al. .......................... 260/210
4,305,961 12/1981 Tsutsumi et al. ........................ 424/361

FOREIGN PATENT DOCUMENTS

95682 A2 12/1983 Germany.

OTHER PUBLICATIONS

Mertz et al Arch. Dermatology, 120(1), 58–62 (Abstract), 1984.

Lang et al Fett Wiss. Technol., 91(9), 363–6 (Abstract), 1989.

*Primary Examiner*—Frederick Krass
*Attorney, Agent, or Firm*—Millen, White, Zelano & Branigan, P.C.

[57] ABSTRACT

This invention relates to a new use of a sophorolipidic compound, of pharmaceutically acceptable salts of the acidic form of the sophorolipid, and of the ester of the deacetylated sophorolipidic acid form as therapeutically active substances in a method for therapeutic treatment of the human or animal body, and more particularly as an activator of macrophages, as a fibrinolytic agent, as a healing agent, as a desquamating agent, and as a depigmenting agent.

11 Claims, No Drawings

UTILIZATION OF SOPHOROLIPIDS AS THERAPEUTICALLY ACTIVE SUBSTANCES OR COSMETIC PRODUCTS, IN PARTICULAR FOR THE TREATMENT OF THE SKIN

This invention relates to a new use of sophorolipids that belong to the group of glycolipids.

Sophorolipids, which are also called sophorosides, are generally obtained by fermentation of a substrate with a suitable bacterial stock. Processes for production of these sophorolipids are described in particular in Patent FR-A-2, 399,438, International Application PCT/FR91/01027, or U.S. Pat. No. 3,205,150 and U.S. Pat. No. 3,312,684 and in the JALS publication, Vol. 65, No. 9, 1988, 1460–1466, Asmer, H., Jetal; "Microbial Production, Structure Elucidation and Bioconversion of Sophorose Lipids." These sophorolipids consist of several classes. In particular, a distinction is made between the lactone forms, which may or may not be acetylated in the 6'-position and 6"-position of sophorose, and the acid forms, which may or may not be acetylated in the 6'-position of sophorose. The lipidic chain varies depending on the chain length of the acids that comprise it, the number and the locations of nonsaturations, and the position of hydroxylation.

Patent Application WO 95/34282 describes and gives examples of sophorolipids as protective agents for the hair and skin and particularly for its anti-radical-type and anti-elastic properties.

U.S. Pat. No. 4,305,961 describes a cosmetologic composition that comprises, as a moistening agent, etherified hydroxyalkyl groups in all of the secondary alcohol functions and in the acetylated sophorolipid groups. Finally, Inoue, in Proc. World Conf. Biotechnol. Fats Oil, Ind., 1988, 206-9 "Bio-surfactants in Cosmetic Applications," describes sophorolipids as moistening the skin.

Sophorolipids have already been used in lactone form in cosmetics for the treatment of hair to combat dandruff, as Patent EP-B209,783 describes it, and as a bacteriostatic agent in deodorants.

In short, these documents describe cosmetologic applications of sophorolipids.

The object of this invention is to show that sophorolipids also have elevated biological activities that turn out to be particularly advantageous for the treatment of skin in general and in particular for the treatment of wounds and for treatment of the skin for aesthetic or therapeutic purposes.

For this purpose, the invention relates to a sophorolipidic compound that corresponds to general formulas (1) or (2), in which R1 represents hydrogen or an acetyl group and R2 represents hydrogen or an alkyl radical that comprises 1 to 9 carbon atoms, when R3 is a saturated radical that contains hydrocarbons with 7 to 16 carbon atoms, or else R2 represents hydrogen or a methyl group when R3 is an unsaturated radical that contains hydrocarbons with pharmaceutically acceptable salts of the compound of formula (1) so that they can be used as therapeutically active substances in a method for therapeutic treatment of the human or animal body.

The invention also relates to a sophorolipidic compound of general formula (1) that has undergone deacetylation and esterification of the carboxylic group so that it can be used as a therapeutically active substance in a method of therapeutic treatment for the human or animal body.

The invention relates more particularly to the use of this sophorolipidic compound as an active substance in the treatment of the skin.

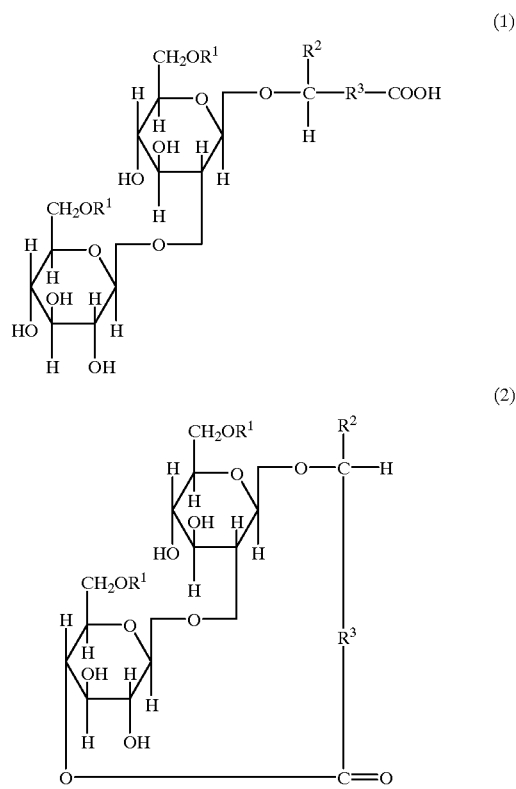

According to preferred embodiments of the invention, this sophorolipidic compound can be used as an activator of macrophages, as a fibrinolytic agent, as a healing agent in particular in the treatment of wounds, or as an agent that promotes desquamation because of its effect on the cohesion of the corneocytes, or as a depigmenting agent, or else as a partial inhibitor of melanogenesis in particular for the treatment of brown spots.

The invention also relates to pharmaceutical compositions that are characterized in that they contain a pharmaceutically inert excipient and as an active ingredient contain at least one compound that is represented by formulas (1) or (2) that are indicated above, a salt of at least one compound of formula (1) that is indicated above, or at least one deacetylated compound of formula (1) of which the carboxylic group is esterified.

Finally, the invention relates to the use of a compound that is represented by formulas (1) or (2) that are indicated above, a salt of a compound of formula (1), or a deacetylated compound of formula (1) whose carboxylic group is esterified to obtain a cosmetic composition that is intended to promote desquamation or depigmenting of the skin.

The invention will be better understood from reading the following description of the embodiments referenced in the attached tables in which:

Table 1 presents amounts of interleukin-1 that are released by macrophages according to the tested products;

Table 2 shows the action of fibrinolysis in vitro;

Tables 3A and 3B present the toxicity of the products of the invention with respect to the different types of cells;

Table 4 presents the results of a desquamation test, and

Table 5 presents the results of a dosage test of melanine in melanocytes that were brought into contact with the products of the invention.

As formulas (1) and (2) that were developed above show, the lipidic portion of the sophorolipids may vary. Furthermore, these sophorolipids generally are in the form of a mixture of various sophorolipids. The most abundant hydroxy fatty acid, however, is 17-hydroxyoctadec-9-enoic acid, also called 17-hydroxyoleic acid. Consequently, all of the tests cited below are carried out with a sophorolipid in acid form that is represented by formula (a) or with a sophorolipid in lactone form that is represented by formula (b).

Sophorolipid (a) could also have been used in the form of a salt or an ester. Actually, at least partial esterification on H+ resins of the carboxylic group of a deacetylated sophorolipid of formula (1) can be accomplished by alcohols such as methanol, which leads to obtaining methyl esters of the totally deacetylated acid form. Depending on the nature of the compounds

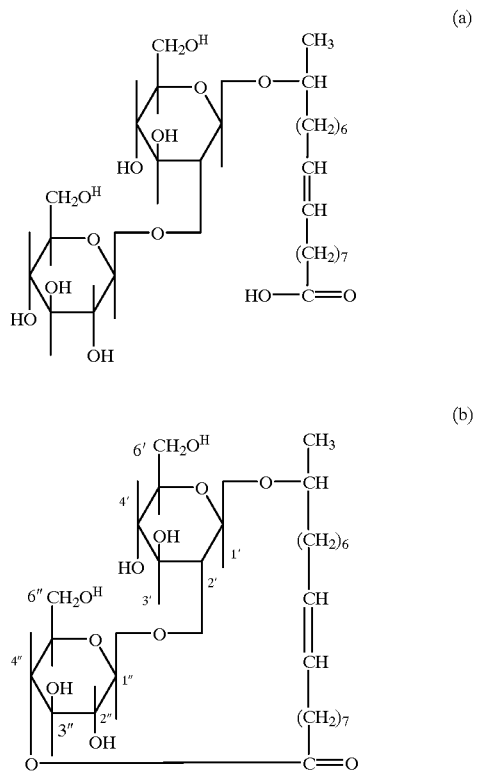

of the mixture, this esterification can be preceded by essentially total deacetylation and delactonization of sophorolipids by saponification, followed by neutralization. The sophorolipid can also be in the form of an alkaline or alkaline-earth metal salt such as Na, Ca or Mg.

The inventor of this invention has found that the sophorolipids of this invention have a pro-inflammatory activity since they show a strong capability of activating monocytes and macrophages in vitro that is objectivized by the release of IL-1. It is known, however, that several factors such as cytokines and growth factors play important roles in the process of wound healing. These factors include the epidermal growth factor (EGF), the fibroblastic growth factor (FGF), the platelet-derived growth factor (PDGF), and the beta transforming growth factor (beta-TGF). In addition to these factors, cytokines such as interleukin-l (IL-1), the tumor necrosis factor (TNF), and interleukin-6 (IL-6) also play important roles in the process of wound healing. These factors act by different methods, in combination with other materials, to induce proliferation of dermal and epidermal elements such as fibroblasts. The biological effects of interleukin-1 are pleiotropical, hence its advantage. Actually, IL-1 affects the differentiation, growth, and activity of many cellular types in the organism. Within the immune system, IL-1 acts as a second signal that is necessary to activate the IL-2 circuit by the activated T lymphocytes. It also potentiates the action of other cytokines. It contributes to the differentiation of B lymphocytes and to their production of immunoglobulins. It modifies vascular permeability by the release of mediators by the endothelial cells and induces the appearance at their surface of a factor that has a procoagulating activity. Owing to its proliferative effect on the fibroblasts, it intervenes in the repair phase.

To show the effect of activating macrophages by sophorolipids, an Elisa sandwich test was carried out on the supernatant of a culture medium that contained macrophages. This test, which was carried out with, for example, an Inter Test 1×X kit (filed trademark), shows the effect of sophorolipids on the release of Interleukin-1 by macrophages. The Interleukin-1 concentrations that are released because of, respectively, the presence of an acid sophorolipid and a sophorolipid in lactone form are specified in Table 1. By way of comparison, the concentration of interleukin IL 1 that is obtained by the action of lipopolysaccharides that are considered as reference products is also indicated. A negative test was also used. It is noted that in their acid form sophorolipids have, at a concentration of $10^{-5}$ M, an action that is equivalent to that of lipopolysaccharides, while they have an action twice that of lipopolysaccharides at a concentration of $10^{-4}$ M. This test clearly shows the capability of sophorolipids as activators of macrophages to induce the release of cytokines. Because of their ability to induce release by the macrophages of the immune system, various interleukins, cytokines, and growth factors simultaneously, sophorolipids can be used as a medicine, as a dressing, or as an active substance for treating wounds generally in connection with topical application. These sophorolipids can be applied to any type of wound. As examples, it is possible to cite, as a nonexhaustive list, traumatic or surgical wounds such as sutures, oozing wounds which may (bedsores) or may not be chronic, varicose wounds or ulcers, "artéritiques" wounds . . .

For the treatment of wounds, all of the galenical forms that are known to date can be considered. Thus, as examples, the sophorolipids can be included in gels or ointments that are to be spread on the wound; in solid matrices, particularly hydrocolloids; in unwoven alginates; in gases that are themselves used in covering wounds. Powders or granulates that contain sophorolipids combined with a matrix (dextranomere, calcium alginate, collagen . . . ) can also be formulated to cover wounds by dusting. Also, these sophorolipids can be combined with standard adjuvants with a formulation like that of viscosity-promoting polymers, stabilizing agents, antioxidants, osmolality regulators, and buffers for forming pharmaceutically acceptable compositions.

By activating macrophages, sophorolipids induce the release of various cytokines, one of whose roles is also to increase the engagement of monocytes that are circulating (chemotactism) at the wound. In addition to their activity on the other cellular radicals by means of cytokines, the activated macrophages ensure the phagocytosis of bacteria, cells, and cellular fragments that obstruct the wound. This detersive action is essential for favorable change in a wound. In particular, chronic wounds such as bedsores have a necrotic fibrous deposit that must be eliminated to allow the wound to granulate and thereby begin healing. The same holds true for other types of wounds where the absorption of exudates and necrotic organic tissue fragments promotes granulation. Sophorolipids therefore make it possible to indirectly cleanse the wound by stimulating macrophages.

They also act directly on necrotic plaque. Actually, the inventor has noted that sophorolipids had a fibrinolytic activity that was objectivized in vitro by the follow-up of lysis by a fibrin clot. This lysis was measured from a fibrin clot that was reconstituted with bovine thrombin and human fibrinogen. The clot that is obtained is covered by 0.5 ml of PBS that contains the sample. The modification of the fibrin gel thickness at 4 hours and 24 hours makes it possible to quantify the fibrinolytic activity. The results, expressed as a percentage of lysis, are summarized in Table 2. This activity will therefore promote fibrinolysis at wounds, making it possible to act on the bedsore spot and to induce better granulation, as well as better organic tissue oxygenation. Moreover, owing to their surfactant property, sophorolipids make the fragments, molecules, soluble and detach the dead cells from the bed of the wound. This last action is more particularly due to their role in desquamation, which will be described below.

The combined actions of fibrinolysis, surfactant cleansing, and macrophagic stimulation make the sophorolipids of the invention useful active molecules for the production of dressings, medicines, and pharmaceutical compositions that are intended in particular for the cleansing phase of wounds.

Their innocuousness and their activity make it possible to use them in other stages of healing, namely granulation and epithelialization, by modulating their concentration in the formulas of products that are used. This is possible only because of the low cytotoxicity of sophorolipids, as Tables 3A and 3B show. The toxicity of the products of the invention has been evaluated with a viability test with neutral red on two cellular types of the skin, cells L929 and other fibroblasts of the dermis and cells NCTC 2544 and keratinocytes of the epidermis. The results, which are presented in Tables 3A, 3B, correspond to the rates of cellular viability that are expressed in % relative to the negative test. Thus, for example, in Table 3A, the sophorolipid in acid form allows, at a concentration of $10^{-6}$ M, 99.65% of the fibroblasts that are initially present to remain alive. These results show that the acid form is 10 times less toxic than the lactone form. This characteristic turns out to be particularly advantageous because of the properties that were already shown in Table 1. This property suggests that the sophorolipids in acid form could prove more advantageous than the lactone form for wound treatment.

Examples 1 to 3a below correspond to three pharmaceutical compositions with each having a different galenical form and each being used at a different stage of healing.

The pharmaceutical compositions usually have a concentration of 0.01 to 5% by weight of sophorolipidic compound (dry material). However, the range of concentrations that is conceivable within the framework of such compositions can be between 0.01 and 35% by weight of dry material.

EXAMPLE 1

The composition below corresponds to that of a gel that is used in the cleansing phase:

Purified water, sufficient quantity for 100
carbomer 940 1%
tromethamine 0.8%
polyvinylpyrrolidone 1%
sodium chloride 0.6%
imidazolidinylyl urea 0.3%
citric acid 0.1%
sophorolipid 0.01–5%
panthenol 0.6%
glutamic acid 1%
methylparaben 0.2%
sodium benzoate 0.2%
potassium sorbate 1%
acemannan hydrogel 4%
sodium metabisulfite 0.3%

EXAMPLE 2

The composition below corresponds to that of a hydrogel that impregnates a compress that is used during the granulation stage.

Propylene glycol alginate 5%
polyquaternium-20 0.1%
sophorolipid 0.01 to 5%
purified water, sufficient quantity for 100

EXAMPLES 3 and 3a

The compositions below correspond to those of a hydrogel that is applied in the form of a membrane on a polyurethane film, with the unit being used during the epithelialization phase.

EXAMPLE 3

Acemannan 5%
xanthane 1%
polyquaternium-10 2%
sophorolipid 0.01 to 5%
potassium gluconate 0.2%
purified water, sufficient quantity for 100

EXAMPLE 3a

Sophorolipid 0.01 to 5%
lipoic acid 0.05%
potassium sorbate 0.1%
purified water, sufficient quantity for 100

In parallel to this action of sophorolipids in the treatment of wounds, the inventor of this invention has noted that sophorolipids activate physiological desquamation by acting on the detachment of corneocytes. Let us recall that the desquamating action of a product consists in eliminating the surface portion of the protective layer of the epidermis (stratum corneum). This protective layer consists of keratinocytes in the terminal stage of differentiating so-called corneocytes. It was already known that hydroxy acids such as lactic acid do not cause disaggregation of the corneocytes of the upper layers of the stratum corneum as keratolytic agents do. In reality, they reduce the thickness of the horny layer by acting on the corneocytary cohesion at newly formed lower layers. This role has also been demonstrated for sophorolipids in the following experiments. A keratinocyte culture that was placed under conditions that promote the differentiation of cells was selected as a cellular model for the study. The actions of sophorolipids in acid form A, sophorolipids in lactone form B, and lactic acid on the detachment of corneocytes of the selected cellular model were tested in vitro in parallel. The results are presented in Table 4. In each experiment, the mean difference T60–T0 (corneocytes/ml), as well as the proportion of detached corneocytes, expressed in percentage relative to the negative test (%/TN), were determined. The statistical significance (Student test t) of differences between the samples and the negative test is expressed by p, which remains less than 0.001 for all the tests that are carried out. Variation coefficient CV is obtained as follows:

$$CV = \frac{\text{standard deviation}}{\text{mean}} \times 100$$

Cellular viability, measured with the Neutral Red test, is expressed relative to the negative test (%). When a response dose is made, the activity of the product can be defined by the T200 concentration. T200 is the concentration which causes a release of corneocytes twice that observed with the negative test. Table 4 shows that for lactic acid, T200 corresponds approximately to a concentration of $10^{-3}$ M, while it corresponds to a concentration of $10^{-4}$ M for sophorolipids. Sophorolipids are therefore ten times more active than lactic acid. This action on the intercorneocytary cohesion of sophorolipids is accompanied by action on the flexibility of the horny layer and a hydrating action on the epidermis. These sophorolipids can therefore be used in dermatology in a number of indications: ichthyosis, acne, xerosis, peeling . . . , but also in cosmetics as an exfoliant or as an anti-wrinkle product or as a regenerative product. Actually, the therapeutic applications incidentally involve cosmetic applications. These cosmetic applications have been particularly surprising with respect to the cosmetic application that had been described in Patent EP-B209,783. Actually, in this document, sophorolipids were used to combat dandruff. A desquamating product is generally not used, however, to treat dandruff since a paradoxical effect will be obtained. This new application of sophorolipids in cosmetics that is deduced from their use in therapeutics is therefore not obvious with respect to the cosmetic application that is already known. Analogously to what was described above relative to the treatment of wounds, the galenical forms of the pharmaceutical or cosmetic compositions to promote desquamation are diverse. As an example, a cosmetic composition that promotes the desquamation of the skin and that is used as an anti-wrinkle regenerating cream is provided below:

Glyceryl stearate SE 12% ceteareth-12 1% octyldodecanol 10% sophorolipidic acid 0.01 to 5% isopropyl myristate 6% wheat germ oil 4% passion flower oil 3% glycerine 5% water, sufficient quantity for 100

Parallel to this desquamating action, it was also found that the sophorolipidic compounds of the invention can be used as partial inhibitors of melanogenesis and in particular as depigmenting agents or for the treatment of brown spots in therapeutics or in cosmetics. It is noted that cutaneous ageing causes epidermal functions to slow down: melanine no longer comes to the surface of the skin in a homogeneous manner and concentrates inside certain cells, and brown spots appear mainly on the hands, the forearms, and the neckline. By acting on melanogenesis, in particular by reducing the production of melanine, sophorolipids can make it possible to gradually eliminate this pigmentation. This depigmenting action is enhanced by the effect of sophorolipids on the detachment of surface cells because of their desquamating role. To demonstrate this action of sophorolipids, the procedure was as follows: melanocytes A J7 and J 14 are placed in a culture, the melanocytes are recovered, washed (phosphate buffer saline: PBS), and centrifuged (20,000 rpm for 20 minutes at +4° C.). Residues are picked up in PBS/triton X-100 (1% v/v) and sounds for 30 seconds. The cellular lysate is ultracentrifuged (105,000 rpm for 40 minutes at +4° C.). The residue that is obtained is then picked up in 1 ml of PBS. The proportion of protein is determined by the calorimetric method (Biorad) and then adjusted to 1.5 mg/ml. The proportion of melanine is then determined, after hydrolysis by 1N soda, for 4 hours at 90° C., by spectrophotometric reading at 420 nm against a standard range that is produced with a synthesis melanine [Sigma].

These results are expressed in % TN, i.e., in the percentage of increase of synthesis of melanine, calculated as follows:

100-(content of melanine of the tested product×100/content of melanine TN)

TN corresponds to the negative test.

The tested product is either linolenic acid, polyunsaturated fatty acid, or a sophorolipidic acid A. Table 5 shows that, unlike linolenic acid, the sophorolipids in acid form bring about a reduction in the synthesis of melanine. In addition to the applications for treatment of brown spots and for depigmenting skin, several therapeutic or cosmetic applications can be considered. As a result, again, the galenical forms are diverse. An example of an anti-spot cream for hands that is also used in cosmetics or in therapeutics is provided below, however:

Ceteareth 30 13%

PEG 7 glyceryl cocoate 20% paraffin oil 5% glycerine 20% water, sufficient quantity for 100

All of the above-mentioned uses of sophorolipids are implemented only in connection with topical application. It is also found that the pharmaceutical and cosmetic preparations can have very similar, if not identical, forms in some cases of use.

Within the framework of cosmetic applications, the concentration of sophorolipidic compounds according to the invention can reach 0.01 to 35% by weight of dry material.

TABLE 1

| | IL 1 Dosage That Is Released by Macrophages | | |
| --- | --- | --- | --- |
| Negative Test T(-) | Sophorolipid in Lactone Form (B) 10-4M 10-5M 10-6M | Sophorolipid in Acid Form (A) 10-4M 10-5M 10-6M | Lipopolysaccharides at 25 µg/ml |
| Concentrations IL-1 pg/ml 27.5 | 255.4 385.9 345.1 | 795.6 500.8 287.2 | 421.61 |

TABLE 2

FIBRINOLYSIS IN VITRO

| | Lactone Form (30% MS) | Acid Form (10% MS) | Acid Form | | | | |
|---|---|---|---|---|---|---|---|
| | | | 10-1M | 10-2M | 10-3M | 10-4M | 10-5M |
| 4 Hours | 15 | 75 | 66 | 5 | 0 | 0 | 0 |
| 24 Hours | 33 | 90 | 80 | 40 | 20 | 5 | 0 |

Lysis of the fibrin clot that is expressed in % relative to TN

TABLE 3A

CYTOTOXICITY ON PRIMOCULTURES at 24 Hours

| | Sophorolipid in Acid Form | | Sophorolipid in Lactone Form | |
|---|---|---|---|---|
| | FIBRO-BLASTS | KERATI-NOCYTES | FIBRO-BLASTS | KERATI-NOCYTES |
| Test | 100 | 100 | 100 | 100 |
| 10-6M | 99.65 | 99.49 | 100.84 | 99.56 |
| 10-5M | 98.65 | 99.9 | 100.05 | 99.56 |
| 10-4M | 98.35 | 99.3 | 91.15 | 95.89 |
| 10-3M | 85.73 | 86.74 | 5.96 | 6.58 |

Cellular Viability Rate Expressed in % Relative to TN

TABLE 3B

CYTOTOXICITY ON L929 (fibroblasts) AND NCTC2544 (epithelial cells) at 24 Hours

| | Sophorolipid in Acid Form | | Sophorolipid in Lactone Form | |
|---|---|---|---|---|
| | L929 | NCTC2544 | L929 | NCTC2544 |
| 5.10-2M | 5.47 | 6.35 | 5.65 | 5.86 |
| 10-2M | 6.18 | 7.12 | 5.26 | 6.49 |
| 5.10-3M | 7.62 | 8.34 | 5.44 | 6.44 |
| 10-3M | 100.45 | 100.45 | 5.71 | 6.17 |
| 5.10-4M | 99.16 | 99.86 | 6.63 | 8.7 |
| 10-4M | 101.82 | 100 | 86.97 | 85.17 |
| 10-5M | 100.51 | 101.4 | 96.5 | 95.54 |

Cellular Viability Rate Expressed in % Relative to the Negative Test (TN = 100%)

TABLE 4

DESQUAMATING TEST

| | | Sophorolipid in Acid Form | | | Lactic AC | Sophorolipid in Lactone Form | | |
|---|---|---|---|---|---|---|---|---|
| Products | Test | 10-4M | 10-5M | 10-6M | 10-3M | 10-4M | 10-5M | 10-6M |
| T60-T0 | 1167 | 2278 | 1944 | 1555 | 2500 | 2389 | 1833 | 1528 |
| CV % | 14.29 | 4.22 | 4.95 | 12.37 | 6.67 | 4.03 | 9.09 | 3.15 |
| %/TN | 100 | 195 | 167 | 133 | 214 | 205 | 157 | 131 |
| % viability | 100.00 | 98.71 | 99.75 | 99.57 | 99.54 | 99.14 | 100.55 | 98.77 |

TABLE 5

MELANINE DOSAGE IN MELANOCYTES AFTER 7 AND 14 DAYS

| | sophorolipid in acid form | | DHA | DHA |
|---|---|---|---|---|
| | % TN | % TN | % TN | % TN |
| Negative test | 100 | 100 | 100 | 100 |
| 10-4M | 56.2 | 56.8 | 109.75 | 113.6 |
| 10-5M | 65.8 | 86.4 | | |
| 10-6M | 93.6 | 95.4 | | |
| | at day 7 | at day 14 | at day 7 | at day 14 |

% TN = 100 - (Content of melanine of the tested product × 100/Content of melanine of the negative test).

I claim:

1. A method of treatment of a wound which penetrates through the epidermis of a human or animal, comprising applying to the wound an effective amount of a sophorolipidic compound of formulas (1) or (2)

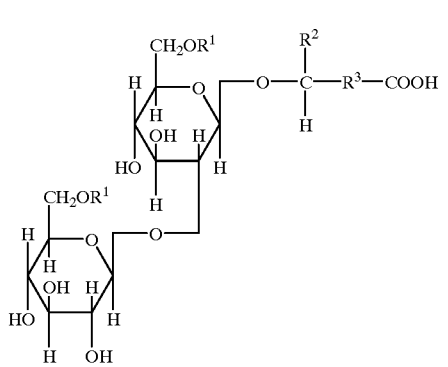

(1)

-continued

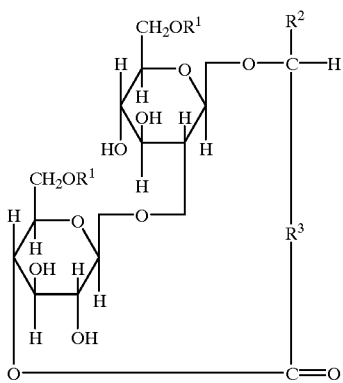
(2)

wherein $R^1$ is hydrogen or an acetyl group and $R^2$ is hydrogen or a $C_{1-9}$-alkyl radical when $R^3$ is a saturated $C_{7-16}$-hydrocarbon radical, or $R^2$ is hydrogen or a methyl group when $R^3$ is an unsaturated $C_{13-17}$-hydrocarbon radical, or a pharmaceutically acceptable salt of the compound of formula (1) or a compound of formula (1) that has undergone deacetylation and esterification of the carboxylic group, whereby said sophorolipidic compound activates macrophages or has a proliferative effect on fibroblasts in the wound.

2. A method according to claim 1, wherein there is employed a sorphorolipidic compound of formula (1) that has undergone deacetylation and esterification of the carboxylic group.

3. A method according to claim 1, wherein macrophages in or below the epidermis are activated.

4. A method according to claim 1, wherein fibrinolytic activity in or below the epidermis is effected.

5. A method according to claim 1, wherein healing activity in or below the epidermis is effected.

6. A method according to claim 1, wherein desquamating activity in or below the epidermis is effected.

7. A method according to claim 1, wherein melanogenesis in or below the epidermis is inhibited.

8. A method according to claim 1, wherein macrophages are activated, fibrinolytic activity is effected and healing activity is effected.

9. A method according to claim 8, wherein there is employed a sophorolipidic compound of formula (I) that has undergone deacetylation and esterification of the carboxylic group.

10. A method of claim 1, wherein said wound is a traumatic or surgical wound.

11. A method of claim 1, wherein said wound is an ulcer, varicose wound or bedsore.

* * * * *